United States Patent [19]

Abruscato et al.

[11] Patent Number: 4,774,374

[45] Date of Patent: Sep. 27, 1988

[54] STABILIZED VINYL AROMATIC COMPOSITION

[75] Inventors: Gerald J. Abruscato, New Britain; Elmar H. Jancis, Naugatuck; Paul E. Stott, Sandy Hook, all of Conn.

[73] Assignee: Uniroyal Chemical Company, Inc., Middlebury, Conn.

[21] Appl. No.: 61,855

[22] Filed: Jun. 12, 1987

[51] Int. Cl.⁴ .................. C07C 7/20; C09K 15/18; C09K 15/20

[52] U.S. Cl. .......................... 585/24; 585/5; 252/401; 252/403

[58] Field of Search .............. 585/24, 5; 252/401, 252/403

[56] References Cited

U.S. PATENT DOCUMENTS

| | | | |
|---|---|---|---|
| 2,399,340 | 4/1946 | Franz | 202/57 |
| 2,526,567 | 10/1950 | Drake et al. | 260/650 |
| 4,105,506 | 8/1978 | Watson | 203/9 |
| 4,457,806 | 4/1984 | Grivas et al. | 203/9 |
| 4,466,905 | 8/1984 | Butler et al. | 252/401 |

FOREIGN PATENT DOCUMENTS 162769 3/1952 Australia ................ 585/24

OTHER PUBLICATIONS

Chem. Abstracts, 140737p, vol. 82, p. 17 (1975) (Yamamoto et al.).
Dweik et al., "Mechanisms of Antioxidant Action...", Rubber Chemical Technology, vol. 57, pp. 735–743 (1984).

*Primary Examiner*—Patrick P. Garvin
*Assistant Examiner*—George R. Fourson
*Attorney, Agent, or Firm*—William E. Dickheiser

[57] ABSTRACT

A vinyl aromatic composition stabilized against polymerization comprising (a) a vinyl aromatic compound and (b) an effective amount of a stabilizer system in which the active ingredient consists essentially of an oxygenated species formed by the reaction of oxygen and an N-aryl-N'-alkyl-p-phenylenediamine. Also disclosed is a process for inhibiting the polymerization of vinyl aromatic compounds employing such an oxygenated species.

15 Claims, No Drawings

STABILIZED VINYL AROMATIC COMPOSITION

FIELD OF THE INVENTION

This invention is directed to a vinyl aromatic composition stabilized against polymerization comprising (a) a vinyl aromatic compound and (b) an effective amount of a stabilizer system in which the active member consists essentially of an oxygenated species formed by reacting a compound of the formula:

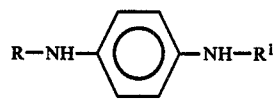

wherein R is $C_6$–$C_{10}$ aryl or $C_7$–$C_{16}$ alkaryl; and $R^1$ is a $C_1$–$C_{12}$ alkyl or $C_3$–$C_{12}$ cycloalkyl; with oxygen.

In another aspect, this invention is directed to a process of inhibiting the polymerization of vinyl aromatic compounds employing such an oxygenated species of a phenylenediamine compound.

BACKGROUND OF THE INVENTION

Commercial processes for the manufacture of vinyl aromatic compounds such as monomeric styrene, divinyl benzene and lower alkylated styrenes (such as alpha-methylstyrene and vinyltoluene) typically produce products contaminated with various impurities, such as benzene, toluene and the like. These impurities must be removed in order for the monomer product to be suitable for most applications. Such purification of vinyl aromatic compounds is generally accomplished by distillation.

However, it is well known that vinyl aromatic compounds polymerize readily and that the rate of polymerization increases rapidly as the temperature increases. In order to prevent polymerization of the vinyl aromatic monomer under distillation conditions various polymerization inhibitors have been employed.

In general, the compounds which are commercially employed as such polymerization inhibitors are of the dinitrophenolic class. Thus, for example, Drake et al, in U.S. Pat. No. 2,526,567, show the stabilization of nuclear chlorostyrenes employing 2,6-dinitrophenols. Similarly, U.S. Pat. No. 4,105,506, to Watson, discloses the use of 2,6-dinitro-p-cresol as a polymerization inhibitor for vinyl aromatic compounds.

More recently, it has been disclosed by Butler et al, in U.S. Pat. No. 4,466,905, that, in the presence of oxygen, the presence of phenylenediamines in the distillation column with 2,6-dinitro-p-cresol will further reduce the amount of polmyerization which occurs.

While dinitrophenols are effective polymerization inhibitors, there are several disadvantages associated with their use, either alone or in blends. For example, dinitrophenols are solids that, if subjected to temperatures above their melting points, are unstable and may explode (see U.S. Pat. No. 4,457,806).

Moreover, dinitrophenols are highly toxic, having an $LD_{50}$(rat) of less than 30 mg/Kg (Sax, Hazardous Properties of Industrial Chemicals).

The high toxicity and low solubility of such dinitrophenolic inhibitors coupled with the flammability of the solvents employed render the shipment and storage of solutions of dinitrophenolic inhibitors in their preferred solvents expensive and somewhat hazardous. Further, if the inhibitor precipitates from solution due to low temperatures during shipment or storage, the actual concentration may fall far below the stated concentration. If such inhibitor solution gets charged to a vinyl aromatic distillation column on the basis of its stated concentration, the low level of inhibitor actually reaching the distillation column can result in catastrophic failure of the distillation column due to explosive polymerization of the vinyl aromatic monomer.

While mixtures such as those described in U.S. Pat. No. 4,466,905 will prevent the polymerization of vinyl aromatics, it would be desirable to possess polymerization inhibitors which would more effectively delay the onset of polymerization and which would avoid the use of highly toxic compounds such as dinitrophenols.

Accordingly, it is an object of this invention to provide an improved inhibitor for the prevention of polymerization of vinyl aromatic compounds.

It is an additional object of this invention to provide an inhibitor for the prevention of polymerization of vinyl aromatic compounds, which inhibitor does not comprise toxic compounds such as dinitrophenols.

It is yet another object of this invention to provide an improved process for inhibiting the polymerization of vinyl aromatic compounds.

The foregoing and additional objects will become more fully apparent from the following description and accompanying Examples.

DESCRIPTION OF THE INVENTION

In one aspect, this invention is directed to a vinyl aromatic composition stabilized against polymerization comprising (a) a vinyl aromatic compound and (b) an effective amount of a stabilizer system in which the active member consists essentially of an oxygenated species formed by reacting a compound of the formula:

wherein R is $C_6$–$C_{10}$ aryl or $C_7$–$C_{16}$ alkaryl; and $R^1$ is $C_1$–$C_{12}$ alkyl or $C_3$–$C_{12}$ cycloalkyl; with oxygen.

In another aspect, this invention relates to a process for inhibiting the polymerization of a vinyl aromatic compound comprising adding to the vinyl aromatic compound an effective amount of a stabilizer system in which the active member consists essentially of an oxygenated species formed by reacting a compound of the formula:

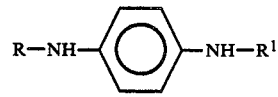

wherein R is $C_6$–$C_{10}$ aryl or $C_7$–$C_{16}$ alkaryl; and $R^1$ is $C_1$–$C_{12}$ alkyl or $C_3$–$C_{12}$ cycloalkyl; with oxygen.

The compositions of this invention are comprised of (a) a vinyl aromatic compound and (b) an oxygenated species formed by the reaction of a specified class of phenylenediamine compounds with oxygen.

Illustrative of the vinyl aromatic compounds which may be stabilized against polymerization by the process of this invention are styrene, alpha-methylstyrene, vinyltoluene and divinylbenzene.

The phenylenediamine compounds which are reacted with oxygen to form the oxygenated species employed in the composition of this invention are of the formula:

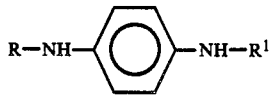

wherein R is $C_6$–$C_{10}$ aryl or $C_7$–$C_{16}$ alkaryl; and $R^1$ is $C_1$–$C_{12}$ alkyl or $C_3$–$C_{12}$ cycloalkyl. Preferably, R is phenyl and $R^1$ is $C_3$–$C_8$ alkyl. Illustrative preferred phenylenediamine compounds which may be employed include N-phenyl-N'-isopropyl-p-phenylenediamine, N-phenyl-N'-(1,3-dimethylbutyl)-p-phenylenediamine, N-phenyl-N'-(1,4-dimethylpentyl)-p-phenylenediamine and N-phenyl-N'-cyclohexyl-p-phenylenediamine. Moreover, mixtures of phenylenediamine compounds may be employed.

The oxygenated species employed in the practice of this invention are formed by the reaction of oxygen with such phenylenediamine compounds. The oxygen may be in gaseous form (such as air or gaseous oxygen) or in the form of an oxygen donor (such as m-chloroperoxybenzoic acid and the like). Preferably, the oxygen is in the form of air.

When gaseous oxygen is employed, the oxygenated species is typically prepared by passing the oxygen through the phenylenediamine at elevated temperatures, generally at least about 50° C., preferably at least about 75° C., up to the decomposition temperature of the activated species. The decomposition temperature of a given species may be determined by routine experimentation by one of ordinary skill in the art. Reaction times will vary in accordance with a number of factors including reaction temperature, the concentration of oxygen in the gas, the particular phenylenediamine and the like, but optimum conditions for any given set of reaction parameters may be determined by routine experimentation. (Routine experimentation generally involves periodically taking samples of the product and evaluating the efficacy of such samples as inhibitors.) The oxygenation reaction may take place in the presence of a hydrocarbon solvent such as benzene, toluene, xylene, ethylbenzene and other alkyl-benzenes, all of which materials are commercially available. Alternatively, the vinyl aromatic compound to be stabilized may be employed as a solvent for the oxygenation reaction.

When the oxygen is in the form of an oxygen-donor compound the reaction parameters will vary in accordance with the particular oxygen-donor compound employed. For example, when m-chloroperoxybenzoic acid is employed, processes such as those described in Dweik et al, "Mechanisms of Antioxidant Action: Aromatic Nitroxyl Radicals and Their Derived Hydroxylamines as Antifatigue Agents for Natural Rubber", Rubber Chemical Technology, Vol. 57, pages 735–743 (1984), may be employed.

The compositions of this invention comprise an effective amount of such an oxygenated species. As employed herein, the term "effective amount" refers to that amount of stabilizer which is needed to prevent the formation of more than about 1 weight percent of vinyl aromatic polymer in less than about 3 hours at temperatures of between about 90° and about 150° C. Although the amount of stabilizer required will vary somewhat (based upon such factors as the particular vinyl aromatic compound stabilized; the particular oxygenated species employed; and the like) such an effective amount may be readily determined by routine experimentation. In general, such an effective amount will be between about 50 and about 1,500 parts per million by weight of vinyl aromatic compound.

The compositions of this invention may further comprise an aromatic hydrocarbon solvent. Illustrative of such solvents are benzene, toluene, xylene, ethylbenzene and other alkyl-benzenes. Typically, when solvents are employed the hydrogenated precursors of the vinyl aromatic to be stabilized are the preferred solvents. Thus, for the stabilization of styrene, ethylbenzene is the preferred solvent. Similarly for the stabilization of alpha-methylstyrene, isopropylbenzene is the preferred solvent.

The process of this invention involves adding to a vinyl aromatic compound an effective amount of an oxygenated species produced by the reaction of oxygen with certain phenylenediamine compounds. This addition may involve the direct injection of a composition comprising such oxygenated species into the vinyl aromatic compound, either prior to or concurrently with the introduction of the vinyl aromatic compound into a distillation column, or by the in situ formation of such oxygenated species by the addition of oxygen (in either gaseous or chemically bound form) to a composition comprising the vinyl aromatic compound and the phenylenediamine compound.

The composition of this invention possesses stability against vinyl aromatic polymerization occurring at temperatures typically employed for the purification of vinyl aromatic compound (e.g., of between about 90° and about 140° C.) for periods well in excess of those typically employed for such purification. This stability is achieved without the use of undesirably toxic chemicals such as dinitrophenols.

EXAMPLES

The following Examples are intended to further illustrate the present invention and are not intended to limit the scope of the invention in any manner whatsoever.

EXAMPLE 1 AND COMPARATIVE EXPERIMENTS A–C

Four 50 ml reaction flasks were prepared a follows. A first flask (Comparative Experiment A) was charged with 40 grams of styrene to which were added 100 ppm dinitro-p-cresol ("DNPC"). A second flask (Comparative Experiment B) was charged with 40 grams of styrene to which was added 50 ppm of DNPC and 50 ppm of N,N'-bis(1,4-dimethylpentyl)-p-phenylenediamine ("BDPD"). A third flask (Comparative Experiment C) was charged with 40 grams of styrene to which was added 50 ppm of dinitro-butylphenol ("DNBP") and 50 ppm of 4-isopropylamino diphenylamine ("IADA"). A fourth flask (Example 1) was charged with 40 grams of styrene to which was added 100 ppm of 4-isopropylamino diphenylamine. The flasks were fitted with magnetic stirrers and septum closures and heated in an oil bath to 118° C. (plus or minus 2° C.). Each flask was purged with approximately 5 cc/min air run beneath the liquid surface during the period of the test. During the test period, samples were removed from each flask every one-half hour and tested for degree of polymerization by measuring the changes in refractive index. The results of these experiments are shown in Table 1.

TABLE 1

| Example or Comparative Experiment | Inhibitor | Inhibitor Concentration(ppm) | Time (Hrs) to Onset of Polymerization* |
|---|---|---|---|
| A | DNPC | 100 | 1 |
| B | DNPC+ BDPD | 50+ 50 | 3 |
| C | DNBP+ IADA | 50+ 50 | 5 |
| 1 | IADA | 100 | 6 |

*Onset of polymerization is defined as the point at which 1 weight percent of the styrene had polymerized.

The above data indicate that the oxygenated species which is produced in situ by the reaction of oxygen (in the air purge) with IADA provided enhanced stability against polymerization relative to dinitrophenolic inhibitor alone or mixtures of dinitrophenolic inhibitors with a diphenylamine.

EXAMPLES 2-4 AND COMPARATIVE EXPERIMENT D

A 250 ml reaction flask was charged with 150 grams of 4-isopropyl-amino diphenylamine (IADA). The flask was fitted with a mechanical stirrer and placed in an oil bath at 135° C. The flask was purged with a subsurface addition of 50 cc/min. of air. A sample of the resultant product after 44 hours of such treatment was tested for inhibition activity as described in Example 1 (at a concentration of 100 ppm) except that a subsurface nitrogen purge was used instead of air.

Several other runs (Examples 3 and 4) were conducted at various oxygenation temperatures for the same time period and employing the same procedure. A comparison of these active species and non-oxygenated material (Comparative Experiment D) which was similarly tested is given in Table 2.

TABLE 2

| Example or Comparative Experiment | Oxygen | Oxygenation Temp(°C.) | Time (Hrs) To Onset or Polymerization |
|---|---|---|---|
| D | No | — | 1 |
| 2 | Yes | 135 | 4.5 |
| 3 | Yes | 150 | 3 |
| 4 | Yes | 80 | 3.5 |

The above results indicate that oxygenated species which are prepared prior to their addition to the vinyl aromatic compound will stabilize the vinyl aromatic compound against polymerization even in the absence of oxygen in the distillation column.

EXAMPLES 5-8 AND COMPARATIVE EXPERIMENT E

Five reaction flasks were each charged with 100 grams of styrene, containing 100 ppm of 4-isopropylamine diphenylamine. Each flask was equipped as described in Example 1 and heated in an oil bath at 100° C. Flask one (Comparative Experiment E) was purged with a subsurface addition of 5 cc/min. of nitrogen. Flask two (Example 5) was injected subsurface with 5 cc of air at the beginning of the test and sealed. Flask three (Example 6) was injected subsurface with 10 cc of air at beginning of the test and sealed. Flask four (Example 7) was injected subsurface with 15 cc of air at the beginning of the test and sealed. Flask five (Example 8) was purged with a subsurface addition of 5 cc/min. of air. Samples from each flask were removed and tested as described in Example 1. Results are shown in Table III.

TABLE 3

| Example or Comparative Experiment | Inhibitor Concentration | Air Injection | Time (Hrs) To Onset of Polymerization |
|---|---|---|---|
| E | 100 ppm | None (N2 purge) | 0.5 |
| 5 | 100 ppm | 5 cc, initial injection | 7 |
| 6 | 100 ppm | 10 cc, initial injection | 7 |
| 7 | 100 ppm | 15 cc, initial injection | 7 |
| 8 | 100 ppm | 5 cc/min | 15 |

The data above indicate that even an initial injection of a relatively small amount of oxygen will produce oxygenated species having antipolymerization activity far in excess of the time (of about 3 hours) which styrene is typically commercially purified.

What is claimed is:

1. A vinyl aromatic composition stabilized against polymerization comprising:
   (a) a vinyl aromatic compound and
   (b) an effective amount of a stabilizer system in which the active member consists essentially of an oxygenated species formed by reacting a compound of the formula:

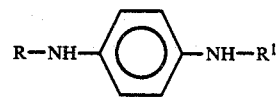

wherein R is $C_6$–$C_{10}$ aryl or $C_7$–$C_{16}$ alkaryl; and $R^1$ is $C_1$–$C_{12}$ alkyl or $C_3$–$C_{12}$ cycloalkyl; with oxygen, said composition being stabilized in the absence of a dinitrophenol compound.

2. A composition in accordance with claim 1 wherein component (a) is selected from the group consisting of styrene, alpha-methylstyrene, vinyltoluene and divinylbenzene.

3. A composition in accordance with claim 1 wherein R is phenyl and $R^1$ is $C_3$–$C_8$ alkyl.

4. A composition in accordance with claim 3 wherein component (b) is the reaction product of oxygen with a member selected from the group consisting of N-phenyl-N'-isopropyl-p-phenylenediamine, N-phenyl-N'-(1,3-dimethylbutyl)-p-phenylenediamine, N-phenyl-N'-(1,4-dimethylpentyl)-p-phenylenediamine and N-phenyl-N'-cyclohexyl-p-phenylenediamine.

5. A composition in accordance with claim 1 wherein component (a) is styrene and component (b) is the reaction product of oxygen and N-phenyl-N'-isopropyl-p-phenylenediamine.

6. A process for inhibiting the polymerization of a vinyl aromatic compound comprising adding to the vinyl aromatic compound an effective amount of a stabilizer system in which the active member consists essentially of an oxygenated species formed by reacting a compound of the formula:

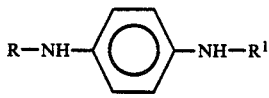

wherein R is $C_6$–$C_{10}$ aryl or $C_7$–$C_{16}$ alkaryl, and $R^1$ is $C_1$–$C_{12}$ alkyl or $C_3$–$C_{12}$ cycloalkyl with oxygen; said process occurring in the absence of a dinitrophenol compound.

7. A process in accordance with claim 6 wherein the oxygenated species is added directly to the vinyl aromatic compound.

8. A process in accordance with claim 6 wherein the oxygenated species is produced by adding oxygen to a composition comprising a vinyl aromatic compound and a compound of the formula:

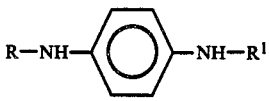

wherein R is $C_6$–$C_{10}$ aryl or $C_7$–$C_{16}$ alkaryl; and $R^1$ is a $C_1$–$C_{12}$ alkyl or $C_3$–$C_{12}$ cycloalkyl.

9. A process in accordance with claim 8 wqherein gaseous oxygen is added at between about 50° C. and the decomposition temperature of such oxygenated species.

10. A process in accordance with claim 8 wherein an oxygen-donor compound is added.

11. A process in accordance with claim 6 wherein said vinyl aromatic compound is selected from the group consisting of styrene, alpha-methylstyrene, vinyltoluene and divinylbenzene.

12. A process in accordance with claim 6 hherein R is phenyl and $R^1$ is $C_3$–$C_8$ alkyl.

13. A process in accordance with claim 12 wherein said oxygenated species is the reaction product of oxygen with a member selected from the group consisting of N-phenyl-N'-isopropyl-p-phenylenediamine, N-phenyl-N'-(1,3-dimethylbutyl)-p-phenylenediamine, N-phenyl-N'-(1,4-dimethylpentyl)-p-phenylenediamine and N-phenyl-N'-cyclohexyl-p-phenylenediamine.

14. A process in accordance with claim 7 wherein said vinyl aromatic compound is styrene and said oxygenated species is the reaction product of oxygen with N-phenyl-N'-isopropyl-p-phenylenediamine.

15. A process in accordance with claim 8 wherein said vinyl aromatic compound is styrene and said oxygenated species is the reaction product of oxygen with N-phenyl-N'-isopropyl-p-phenylenediamine.

* * * * *